United States Patent
Furnas

[11] Patent Number: 6,031,221
[45] Date of Patent: Feb. 29, 2000

[54] CONTAINER INSPECTION MACHINE

[75] Inventor: William J. Furnas, Elmira, N.Y.

[73] Assignee: Emhart Glass S.A., Cham, Switzerland

[21] Appl. No.: 09/026,311

[22] Filed: Feb. 19, 1998

[51] Int. Cl.[7] .................................................. G01N 21/90
[52] U.S. Cl. ..................... 250/223 B; 209/526; 209/524; 356/239.1
[58] Field of Search .......................... 250/223 B, 559.08, 250/559.07, 559.22, 223 R, 552, 553; 209/526, 525, 522, 523, 524; 356/239.1, 239.4, 239.7, 376

[56] References Cited

U.S. PATENT DOCUMENTS 4,500,203  2/1985  Bieringer ............................... 356/239.4
5,059,031  10/1991  Hamel et al. ............................ 356/428
5,486,692  1/1996  Baldwin .............................. 250/223 B

*Primary Examiner*—Edward P. Westin
*Assistant Examiner*—Thanh X. Luu
*Attorney, Agent, or Firm*—Spencer T. Smith

[57] ABSTRACT

A machine is disclosed for inspecting the profile and wall of a bottle which is delivered by a conveyor sequentially to two inspection stations. A pair of light sources, when fully illuminated, define two images of the bottle on a CCD camera image, so that the wall can be inspected. Portions of the light sources are darkened so that two different images of the bottle will be imaged on the CCD camera image so that the profile can be inspected.

5 Claims, 2 Drawing Sheets

CONTAINER INSPECTION MACHINE

The present invention relates to a machine for inspecting glass or plastic containers such as bottles and more particularly to such a machine which can inspect either the sidewall for body defects or the periphery of the bottle for profile defects.

BACKGROUND OF THE INVENTION

The manufacture of glass bottles may produce a profile defect (cocked finish, bent neck, base leaner) or a wall defect (stone, bubble or inclusion) which makes the bottle unacceptable.

Generally the front surface of the bottle will be illuminated so that it becomes transparent. It can then be examined for wall defects. To make a complete examination of the front surface, which extends 360°, a number of angularly related views (usually four) of the front surface are required. U.S. Pat. No. 5,486,692, discloses a state of the art four view system used for inspecting for wall defects. While four views are used for wall defect inspection only two angularly related views are required for profile inspection.

It is an object of the present invention to provide an improved machine for wall and profile inspection.

OBJECT OF THE INVENTION

Other objects and advantages of the present invention will become apparent from the following portion of this specification and from the accompanying drawings which illustrate in accordance with the mandate of the patent statutes a presently preferred embodiment incorporating the principles of the invention.

BRIEF DESCRIPTION OF THE DRAWINGS

FIG. 3 a view taken from the camera looking at a bottle to be inspected with both controlled light sources fully on.

BRIEF DESCRIPTION OF THE PREFERRED EMBODIMENT

Figure 1:
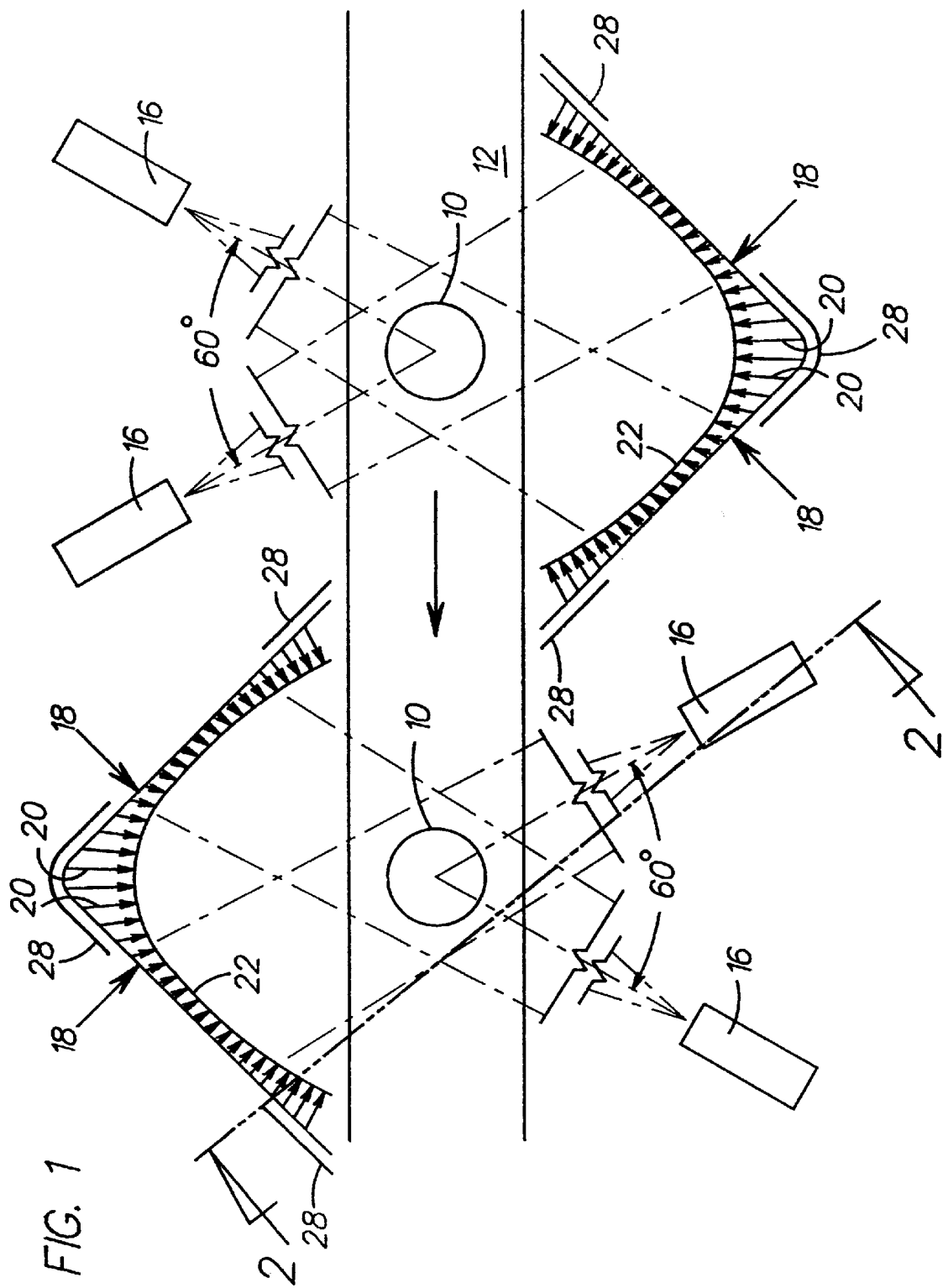
FIG. 1 is a top view of an inspection machine made in accordance with the teachings of the present invention.
Figure 2:
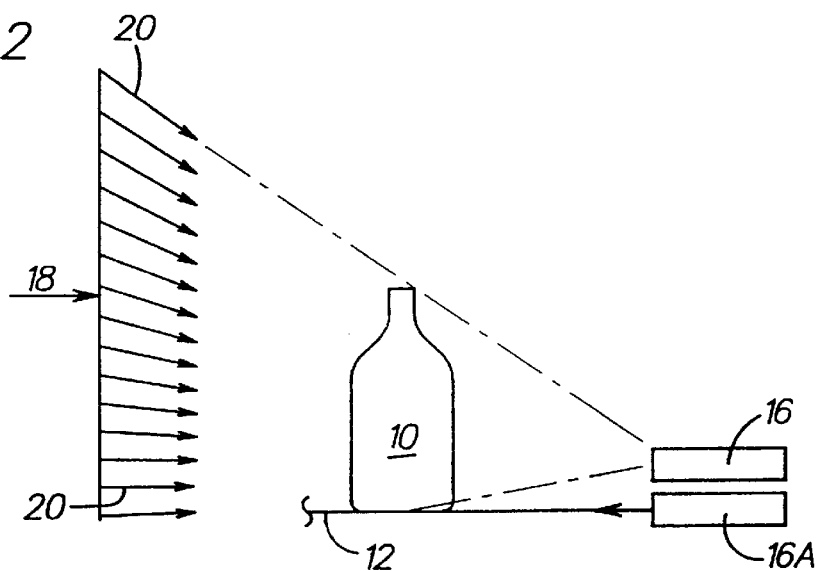
FIG. 2 is view taken at 2—2 of FIG. 1.

A bottle 10, which can be either glass or plastic is conveyed from right to left along a conveyor 12 for sequential inspection at the two illustrated inspection stations shown in FIG. 1. At the first inspection station two angularly related (60° in the illustrated embodiment) views of the bottle are imaged on the image of a CCD camera 16 with the use of suitable beam splitting optics such as disclosed in U.S. Pat. Nos. 4,025,201 and 5,486,692 (one view is imaged on one half the camera image and the other view is imaged on the other half of the camera image). This camera will make a wall inspection of each of the two views. At the second station two angularly related (60° in the illustrated embodiment) views of the bottle are defined to be imaged on the images of a pair of vertically stacked CCD cameras 16, 16A (FIG. 2) with the use of similar beam splitting optics. One camera will make a wall inspection of each of the two views and the other camera will make a profile inspection of the two views.

While in the preferred embodiment both views are simultaneously imaged on the image of a CCD camera, a pair of cameras is shown at each station in FIG. 1, to simplify the illustration of the invention. It is to be understood that optionally a single camera could image each view at each station for each inspection or a single camera could be present at each station with the camera at the second station imaging both views with sequential images taken of the bottle for wall inspection and profile inspection, or a single camera can be used at the first inspection station with a stacked pair of cameras used at the second station each imaging both views, with one camera dedicated to wall inspection and the other dedicated to profile inspection.

Associated with each view is a controlled light source 18 which defines a large area of light with a large number of vertical rows of L.E.D.s 20. As can be seen from FIGS. 1 and 2, the L.E.D.s are focused or aimed so that light will pass through the entire bottle (from top to bottom and from side to side) and be imaged on the camera(s). In a simple design each vertical row of L.E.D.s can be turned on and off with a field effect transistor (not shown). A substantially arcuate or wrapped diffuser 22 intercepts the light from the two controlled light sources thereby diffusing the light and substantially eliminating the dark spacing between the two light sources.

Figure 3:
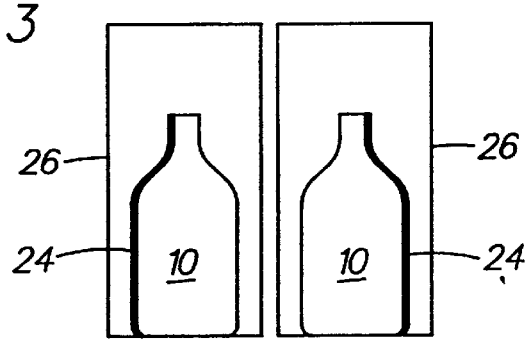
Figure 4:
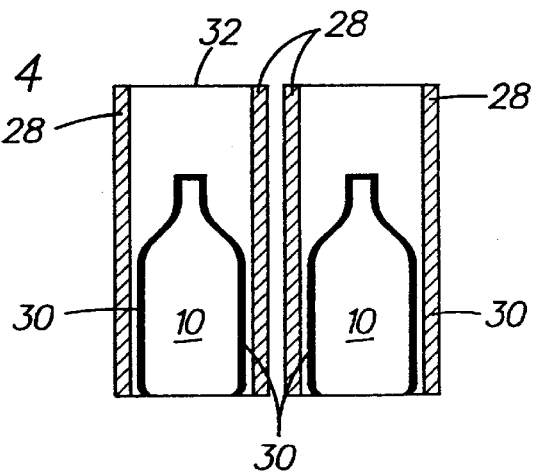
FIG. 4 is a view similar to that of FIG. 3 with portions of the controlled light sources off.

To inspect the sidewall of the bottle at either station, both light sources are illuminated fully (all L.E.D.s turned "on") at a high intensity. In each view of the bottle at the inspection station as shown in FIG. 3, the side 24 of the bottle proximate the edge 26 of the controlled light source panels (both panels viewed as a single item) will appear dark thereby providing a datum for the wall inspection. The rest of the bottle is substantially transparent so that wall defects can be examined.

To inspect the profile of the bottle at the second station, the controlled light sources are illuminated at a lower intensity and one or more vertical rows of L.E.D.s are turned off at either side of each controlled light source (the number of rows at each side of each controlled light source to be turned off can be independently set) to define dark areas 28 behind the side edges 30 of the body of the bottle to present a clear dark profile of the body to the camera (the dark areas are schematically shown as black lines behind the light sources in FIG. 1). Because of the refractive nature of the neck and finish portion 32 of the bottle, the dark areas will also make the profile of the finish appear dark as well. The profile of the bottle, in each view can therefore be analyzed. While the light sources disclosed have vertical rows of lights which can be individually turned on and off to define vertical dark rows, other light sources could be used which would permit a different choice of areas of the source to turn off. In such sources the operator would turn off the areas that would achieve the desired results.

Where stacked cameras are used at the second station, the camera 16A (the profile camera) that will analyze the profile of the bottle is aimed (FIG. 2) so that the conveyor surface will not be seen and the second camera 16 will be located above the profile camera 16A. As can be seen from FIG. 1, the angle between the views is selected to maximize the area of the controlled light sources (the conveyor limits the area in which the controlled light sources can be located) and maximize illumination of the sidewall taking advantage of the effects of the refractive properties of the glass associated with the wall of the bottle, particularly the thicker wall and larger I.D. and O.D. differential in the neck of the bottle.

I claim:

1. A machine for inspecting the profile and wall of a bottle comprising a conveyor for supporting a bottle at a first inspection station, CCD camera means on one side of the conveyor having first camera image means, a first light source, having an illumination area, on the other side of the conveyor, for imaging the bottle on said CCD camera image means, said first light source operable to illuminate the entire illumination area to illuminate the bottle at the inspection station so that the wall of the bottle imaged on said CCD camera image means will appear substantially transparent, and said illumination area having selected portions which are turned off when the light source is operated to present a dark the profile of the bottle to said CCD camera image means.

2. A machine for inspecting the profile and wall of a bottle according to claim 1, wherein said light source includes a plurality of vertical rows of L.E.D.s and wherein individual rows of said L.E.D.s can be turned off.

3. A machine for inspecting the profile and wall of a bottle according to claim 2, wherein said CCD camera means comprises a first CCD camera having a first camera image for imaging the bottle when said light source operates to illuminate the entire illumination area and a second CCD camera having a second camera image for imaging the bottle when said selected portions of the illumination area are turned off.

4. A machine for inspecting the profile and wall of a bottle according to claim 3, further comprising a second light source, having an illumination area, on the other side of the conveyor, for imaging the bottle at the first inspection station on said first and second camera images, said second light source operable to illuminate the entire illumination area to illuminate the bottle at the inspection station so that the wall of the bottle imaged on said first camera image will appear substatially transparent, and said illumination area of said second light source having selected portions which are turned off when the light source is operated to present a dark profile of the bottle to said CCD camera means.

5. A machine for inspecting the profile and wall of a bottle according to claim 4, wherein said second light source includes a plurality of vertical rows of L.E.D.s and wherein individual rows of said L.E.D.s can be turned off when said light source is operated.

* * * * *